Figure 1:
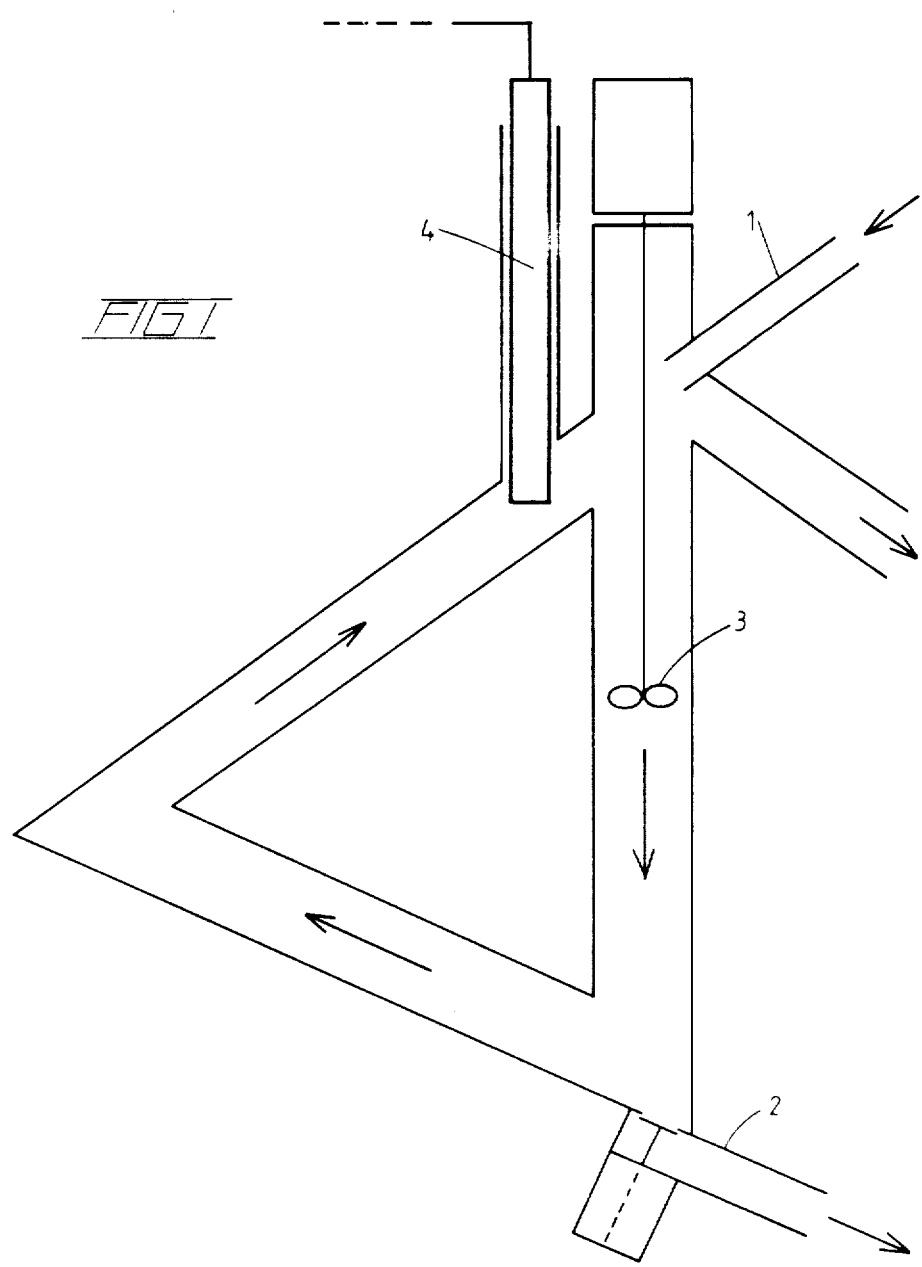

United States Patent [19]
Bond et al.

[11] Patent Number: 4,504,367
[45] Date of Patent: Mar. 12, 1985

[54] MONITORING OF CHEMICAL SPECIES IN SOLUTION AND APPARATUS THEREFOR

[75] Inventors: Alan M. Bond, Toorak; Henry A. Hudson, Queenscliff; Pierre A. van den Bosch, Portarlington; Frederick L. Walter, Belmont, all of Australia

[73] Assignee: Deakin University, Australia

[21] Appl. No.: 495,237

[22] Filed: May 16, 1983

[30] Foreign Application Priority Data

May 14, 1982 [AU] Australia .................. PF4018/82

[51] Int. Cl.$^3$ ............................................ G01N 27/28
[52] U.S. Cl. .................................. 204/1 T; 204/409
[58] Field of Search ............... 204/409, 418, 419, 420, 204/1 T

[56] References Cited

U.S. PATENT DOCUMENTS

| | | | |
|---|---|---|---|
| 3,616,272 | 10/1971 | Goerg et al. ..................... | 204/1 T |
| 3,809,637 | 5/1974 | Higashiyama et al. ............. | 204/419 |
| 4,409,088 | 10/1983 | Kanno et al. ..................... | 204/402 |

OTHER PUBLICATIONS

Josef Vesel et al., "Analysis with Ion-Selective Electrodes", pp. 194–197, (1978).
W. J. Blaedel et al., Anal. Chem., vol. 47, No. 7, pp. 1070–1073, Jun. 1975.
E. A. Ostrovidov, Ind. Lab., vol. 42, No. 9, pp. 1370–1371, (Sep. 1976).

Primary Examiner—G. L. Kaplan
Attorney, Agent, or Firm—Sughrue, Mion, Zinn, Macpeak and Seas

[57] ABSTRACT

A method and apparatus for determining the concentration of chemical species in solution. The method involves passing the solution through a cell containing an ion-selective electrode. Measurement is carried out following suppression of interfering materials, under turbulent flow conditions. The apparatus preferably includes microprocessor controlled instrumentation and is particularly useful for the on-line determination of the concentration of copper(II) ions in electrolyte solutions.

8 Claims, 2 Drawing Figures

MONITORING OF CHEMICAL SPECIES IN SOLUTION AND APPARATUS THEREFOR

This invention relates to a method and apparatus for determining the concentration of chemical species in solution using an ion-selective electrode. The invention is partially based upon experiments concerned with the determination of the concentration of copper(II) ions in electrolyte solutions and it will therefore be described primarily in that context although it will be readily appreciated that the invention encompasses much broader ambits than this.

In electroplating and electrorefining processes, a knowledge of the concentration levels of the electrolytic components is often required continually to ensure accurate control of those processes. For example, in the electrorefining of copper where continuous purification of the electrolyte solution is required, it is essential during the electrolyte purification that the copper(II) ion concentration be carefully and continually monitored to ensure that it does not drop below a critical concentration at which the poisonous volatile gas, arsine, is produced.

Many methods are available for determining copper(II) ion concentration in electrolyte solutions but most of these methods are unsuitable for continuous on-line monitoring in the previously mentioned process. For instance, copper(II) ion concentration levels are so high that atomic absorption spectrometry and polarography require very large dilutions. The former method is used for the off-line determination of the copper(II) ion concentration. Spectrophotometry has been attempted as an on-line procedure but a high ionic nickel concentration in the electrolyte will cause severe interference. Correction methods for the presence of ionic nickel have been employed but owing to variabilities in the system, the spectrophotometric method is not satisfactory for continuous monitoring of the copper(II) ion concentration.

Ion-selective electrodes are inexpensive and easy to implement for continuous monitoring using microprocessor-based technology. To date, however, they have not been extensively applied to continuous on-line monitoring of chemical species in industry. A possible reason why they have not been employed in monitoring the copper(II) ion concentration in the previously mentioned process may have been due to the interference caused by Fe(III) ions.

It has now been discovered that such interference can be suppressed and that accurate copper(II) ion concentrations can be determined using an ion-selective electrode if the measurements are carried out under specific conditions.

Accordingly, in its broadest aspect, the invention provides a method for determining the concentration of a chemical species in solution using an ion-selective electrode, comprising the steps of:

(i) passing a sample of solution containing the chemical species to be determined into a cell containing an ion-selective electrode, said sample being mixed either prior to or upon entering the cell with a reagent for reducing the interference of unwanted substances with the ion-selective electrode;

(ii) circulating the sample and reagent within the cell under turbulent flow conditions; and (iii) measuring the concentration of the chemical species to be determined while it is circulating in the cell, by means of the ion-selective electrode.

The method is applicable to the determination of the concentration of any chemical species in solution provided that the chemistry to remove any interference can be performed. The method can be used for the measurement of the activity or concentration of any anion (eg. fluoride) or cation (eg. copper(II)) which is sensitive to the appropriate ion-selective electrode. Thus, in the case of copper(II) concentration determination in the previously mentioned copper electrorefining process, the major interfering agent is the iron(III) ion. Methods for iron(III) ion control can be divided into (a) precipitation as the hydroxide (b) complexing, e.g. by fluoride, and (c) reduction. Precipitation and complexing are unsatisfactory because of the presence of other cations, e.g. nickel(II) and calcium(II), and the acid strength of the electrolyte (2-3M sulphuric acid). Other complexing agents are unsatisfactory because the copper(II) is complexed too. Reduction procedures, however, produced very favourable results. The effects of a number of reducing agents were examined. The best result, under the conditions of the determination, was given by ascorbic acid. The presence of 2-3M sulphuric acid does not effect reduction by ascorbic acid. The addition of ascorbic acid removes the interference by the iron(III) ion so effectively that copper(II) readings revert to values of the uncontaminated solutions, thus restoring obedience to the Nernst equation.

Thus the controlled addition of ascorbic acid produces a satisfactory environment in which interference by iron(III) ion or any other species which may oxidise the electrode surface is prevented.

According to a further aspect of the present invention there is provided an apparatus for use in determining the concentration of a chemical species in solution, said apparatus comprising:

(I) a flow-through cell, constructed so as to provide a turbulence producing path for the solution which flows through it;
(II) means to circulate the solution within the cell; and
(III) an ion-selective electrode arranged to project into the circulating solution. Preferably the arrangement is at right-angles to the direction of flow.

The apparatus can be connected to a suitable solution sampling system and may include one or more electrodes for calibration against a standard solution.

The ion-selective electrode and reference electrode are conveniently connected with microprocessor controlled instrumentation for continuous automatic monitoring.

Figure 2:
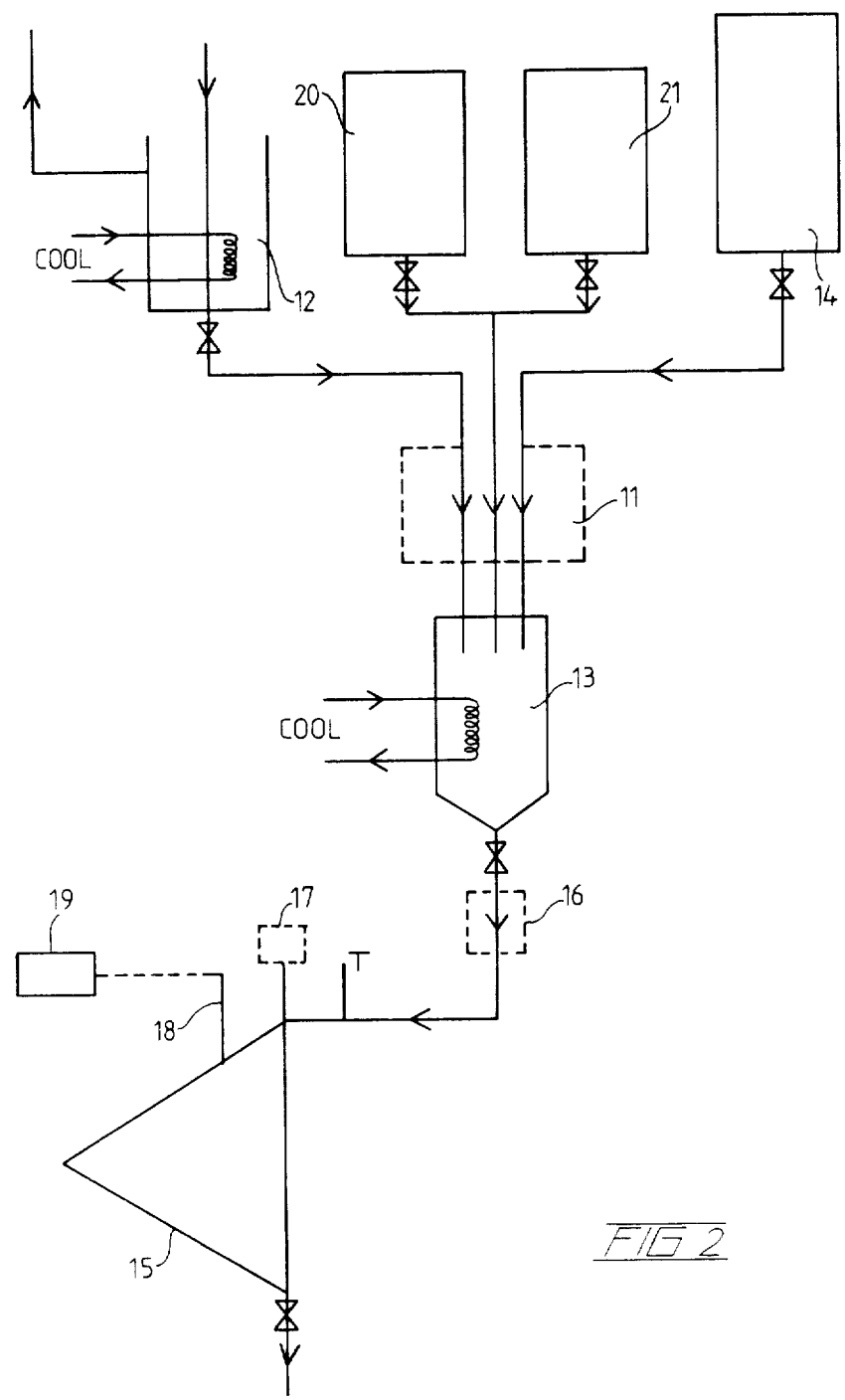

Preferred embodiments of the invention will now be described with reference to the accompanying drawings in which:

FIG. 1 is a schematic representation of an apparatus according to the invention, and FIG. 2 is a flow diagram of a complete system for determining the concentration of chemical species in solution.

Referring firstly to FIG. 1, there is depicted a delta shaped cell construction which has been found to be particularly suitable in establishing the necessary turbulent flow path for the invention to succeed.

A solution containing the chemical species whose concentration is to be determined is passed into the delta cell by way of inlet 1. The position of entry enables the cell to be rinsed rapidly and effectively between samples, and the solution to drain via outlet 2. When the cell is full, turbulent flow circulation is produced by the positive action of a stirrer 3 in conjunction with the cell geometry. A suitable flow rate is above about 1 liter min$^{-1}$ for a 200 ml capacity cell. Sensing and reference electrodes 4 are oriented at an acute angle to the direction of flow as indicated by the arrows. The transverse alignment of the electrodes permits both probes to sense the same solution simultaneously. This arrangement prevents any stream disturbance by the electrodes influencing the determination. The position of the electrodes and the cell shape enable the electrolyte to impinge directly on the ion-selective electrode sensor. The solution is pumped around the cell for a given time to ensure thorough mixing and equilibration of the electrodes before taking potential measurements.

The apparatus depicted in FIG. 1 may be effectively employed in the system depicted in FIG. 2 which is a copper(II) ion monitoring system. Here, a metering pump 11, built of inert material, discharges cooled plant electrolyte from a constant level tank 12 into a mixing chamber 13. Simultaneously a measured amount of ascorbic acid solution from an air-tight reservoir 14 is pumped to the mixing chamber 13 in which further cooling takes place. The treated solution is pumped to the electrochemical measuring delta-shaped cell 15 by the metering pump 16, rinsing the cell of the previous liquor. After completion of the drainage time, the delta cell is filled with new treated electrolyte of a known temperature which is measured at point T and circulated by stirrer 17. After a suitable time interval, the copper(II) ion concentration is determined using the ion-selective electrode 18. Microprocessor controlled instrumentation 19 selects the sequence of events in the cycle and records the data.

Calibration of the delta cell apparatus is performed by using two standard solutions, 20, 21, which differ by a factor of ten in copper(II) ion concentration. An identical cycle is followed for each of the calibrations as for the plant electrolyte.

The monitoring system can be operated manually, but an automated sequence is preferred as the standard instrument procedure. The microcomputer can control the full sequence of events thus:

1. Calibration of the cell using two standard solutions with a factor of ten different in concentration and with a matrix which mimics the plant electrolyte.
2. Treated plant electrolyte rinses the cell immediately following dumping to waste of the standard solution.
3. Outlet is closed. The cell is filled with treated plant electrolyte. The liquor is circulated by the stirrer and the copper(II) ion concentration determined. Outlet is opened.
4. The next batch of plant electrolyte rinses the cell and the cycle continues as before.
5. Copper determinations on the plant electrolyte continue at fixed time intervals until recalibration of the cell is required.
6. In the cell calibration an exactly similar procedure as for the plant electrolyte is followed.

Ascorbic acid solution is ideally stored in a "bag in a box" (as in the wine casks) to ensure anaerobic conditions. The container is purged with high purity nitrogen gas before filling the bag. "Malpas" designed tap and connection is used on the outlet.

We claim:

1. A method for determining the concentration of a chemical species in solution using an ion-selective electrode assembly including sensing and reference electrodes, comprising the steps of:
   (i) passing, a sample of solution containing the chemical species to be determined into a closed-loop cell containing an ion-selective electrode assembly, said sample being mixed either prior to or upon entering the cell with a reagent for reducing the interference of unwanted substances with the ion-selective electrode assembly;
   (ii) recirculating the sample and reagent within the closed-loop cell under turbulent flow conditions; and
   (iii) measuring the concentration of the chemical species to be determined while it is circulating in the cell by means of the ion-selective electrode assembly, said ion-selective electrode assembly having sensing and reference electrodes arranged transversely to the direction of flow of the solution to sense the same portion of the solution simultaneously.

2. A method as claimed in claim 1 when applied to the determination of the anion or cation activity or concentration of a solution.

3. A method for determining the concentration of copper(II) in an electrolyte solution using an ion-selective electrode assembly including sensing and reference electrodes, comprising the steps of:
   (a) passing a sample of the electrolyte solution into a closed-loop cell containing an ion-selective electrode assembly, said sample being mixed upon entering the cell with a reducing agent which prevents interference of unwanted substances with the ion-selective electrode assembly;
   (b) recirculating the sample and the reducing agent within the closed-loop cell under turbulent flow conditions; and
   (c) measuring the concentration of the copper(II) while it is circulating in the cell by means of the ion-selective electrode assembly, said ion-selective electrode assembly having sensing and reference electrodes arranged traversely to the direction of flow of the solution to sense the same portion of the solution simultaneously.

4. A method as claimed in claim 3, wherein the reducing agent is ascorbic acid.

5. An apparatus for use in determining the concentration of a chemical species in solution, said apparatus comprising:
   (I) a flow-through closed-loop cell, constructed so as to provide a turbulence producing path for the solution which flows through it;
   (II) means to recirculate the solution within the cell; and
   (III) an ion-selective electrode assembly including sensing and reference electrodes arranged to project into the circulating solution and further arranged so that the sensing and reference electrodes are traverse to the direction of flow of the solution to sense the same portion of the solution simultaneously.

6. An apparatus as claimed in claim 5, wherein the ion-selective electrode projects into the circulating electrolyte at an acute angle to the direction of flow.

7. An apparatus as claimed in claim 5, wherein the flow-through-cell has a delta-shaped configuration.

8. An apparatus as claimed in claim 5, wherein the means to circulate the solution within the cell is a paddle stirrer projecting into the cell and operated by an external motor.

* * * * *